United States Patent [19]

Hill

[11] 4,318,991

[45] Mar. 9, 1982

[54] BAKER'S YEAST WITH IMPROVED LEAVENING POWER IN ACID DOUGH

[75] Inventor: Frank Hill, Dusseldorf, Fed. Rep. of Germany

[73] Assignee: Henkel Kommanditgesellschaft auf Aktien (Henkel KGaA), Dusseldorf-Holthausen, Fed. Rep. of Germany

[21] Appl. No.: 18,307

[22] Filed: Mar. 7, 1979

[30] Foreign Application Priority Data

Mar. 11, 1978 [DE] Fed. Rep. of Germany ....... 2810601

[51] Int. Cl.$^3$ ............................ C12N 1/36; C12N 1/18
[52] U.S. Cl. ..................................... 435/245; 426/60; 426/62; 435/256
[58] Field of Search ................... 426/60, 62; 435/245, 435/256

[56] References Cited

U.S. PATENT DOCUMENTS

| | | | |
|---|---|---|---|
| 1,464,710 | 8/1923 | Hixson | 435/256 |
| 1,727,847 | 9/1929 | White | 435/245 |
| 1,974,937 | 9/1934 | White | 435/245 X |
| 3,617,306 | 11/1971 | Pomper et al. | 435/256 |
| 3,681,199 | 8/1972 | Rokitansky | 435/256 X |
| 3,922,350 | 11/1975 | Dockendorf et al. | 426/62 X |
| 3,993,783 | 11/1976 | Langejan et al. | 426/60 X |

*Primary Examiner*—David M. Naff
*Attorney, Agent, or Firm*—Hammond & Littell, Weissenberger and Muserlian

[57] ABSTRACT

A process for the production of baker's yeast with improved activity or leavening power under acid leavening conditions is carried out by cultivating fresh yeast conventionally to the last propagation stage, propagating the fresh yeast in the last propagation stage in the presence of from 0.1 gm to 10 gm per liter of culture broth containing a source of carbon and nitrogen, of an aliphatic carboxylic acid having from 2 to 4 carbon atoms, and recovering baker's yeast with improved activity or leavening power.

5 Claims, No Drawings

BAKER'S YEAST WITH IMPROVED LEAVENING POWER IN ACID DOUGH

BACKGROUND OF THE INVENTION

This invention relates to a process for the preparation of compressed baker's yeast or dry baker's yeast with improved activity or leavening power in an acid medium, the compressed baker's yeast or dried baker's yeast prepared by this process and to bread and to pastry products obtained using this baker's yeast.

Compressed baker's yeast and dry baker's yeast prepared by the usual processes generally have a good activity or leavening power in both unsugared and sugared neutral doughs but their leavening power is unsatisfactory in acid doughs in the presence of organic acids such as acetic acid, propionic acid or lactic acid. Below certain pH values, these acids considerably inhibit the fermentation produced by the usual baker's yeasts.

Many types of bread require the presence or use of both the aforesaid acids and baker's yeast for their production. Thus, for example, propionic acid and its salts, which have a fungistatic action in an acid pH, are frequently used in the bread industry to prevent the formation of mold in packaged, sliced bread which can be toasted and as constituents of many baking additives employed in the production of such packaged, sliced breads. In fact, it is only the use of these fungistatic substances which has made it possible for packaged, sliced bread with a long shelf life to be manufactured on an industrial scale.

The packaged, sliced bread designed for toasting has uniform slices with a thin pliable crust in contrast to breads of the European type which are not customarily sold in presliced condition and which usually have a relatively thick, nonpliable crust.

Furthermore, the addition of calcium acetate or acetic acid to the dough is recommended, for example, to prevent a so-called ropiness or stringiness in the manufacture of unacidified bread. In the manufacture of mixed breads containing rye flour, of the types which are particularly common in the Federal Republic of Germany, organic acids are added to the dough or formed during the fermentation process. The organic acids used for this purpose, in this case mostly acetic acid and lactic acid, considerably improve the baking properties of rye flour. Acetic acid and lactic acid are either produced by the bacterial flora during manufacture of these rye mixed breads, for example, when the Berlin short leavening method is used, or they are added directly to the dough in the dry leavening method and the finished leavening method.

The experiments described below are included to demonstrate the reduction in the leavening activity of fresh baker's yeast (compressed yeast) by the addition of acid substances to the dough. Two commercial fresh baker's yeasts A and B, for the bakery trade, were used for the experiments. 1.35 gm of the yeast, based on the content of dry substance in the yeast, were mixed in each case with 280 gm of wheat flour, 3.9 gm of cooking salt and 156 ml of tap water to form a dough. The water was previously warmed up so that the dough was at a temperature of 30° C. after it had been kneaded for 5 minutes. The results of the tests are indicated in Table I below. The quantity of substances added is given in percentages, based on the quantity of flour used. The leavening activity of the yeasts was determined over a period of 2 hours at 30° C. in the Fermentograph manufactured by Brabender, Duisburg, and is given as ml of carbon dioxide.

TABLE 1
Reduction in Leavening Activity of Fresh Baker's Yeast (Compressed Yeast) by Presence of Acid-Reacting Additives in the Dough

| Yeast | Additive | Leavening Activity ml $CO_2$ | % Activity of the Controls |
|---|---|---|---|
| A | — | 1010 | 100 |
| | 0.5% calcium propionate | 600 | 59 |
| | 0.5% calcium acetate | 930 | 92.1 |
| | 1% of 80% lactic acid | 790 | 78.2 |
| B | — | 1050 | 100 |
| | 0.5% calcium propionate | 660 | 62.8 |
| | 0.5% calcium acetate | 910 | 90.1 |
| | 1% of 80% lactic acid | 840 | 80 |

The extent to which the additivies in the dough inhibited the leavening activity of the yeast was approximately the same for both of the commercial fresh baker's yeasts and was in the region of 8% to 41% depending on the type of acid-reacting additive. The inhibitory effect of the additives can be further increased by lowering the pH of the dough. In test doughs containing calcium propionate and calcium acetate as additives, the pH was 6.6; in the test dough containing lactic acid the pH was 4.7. In sour dough, the pH may even fall to 4.0.

When the dough recipe is used which is even closer to that used in practice, to which has been added a commercial baking additive for packaged, sliced bread containing approximately 10% of propionate as calcium propionate, the effect of the presence of the short chain carboxylic acid salt in reducing the leavening power of the yeast is even more significant.

The reduction in leavening activity is particularly pronounced in the case of dry baker's yeast. Substitution of fresh baker's yeast by active dry baker's yeast in this field of bakery products has, therefore, hitherto not been possible owing to the lack of leavening power of dry baker's yeast in doughs which have a high degree of acidity or to which carboxylic acids have been added.

The leavening power of commercial fresh baker's yeast is compared below with that of commercial instant dry baker's yeast in a dough used for the manufacture of mold-proof packaged, sliced bread. For the experiment, a dough was prepared from 1000 gm of type 550 wheat flour, 590 gm of water, 21 gm of dry yeast substance (corresponding to 70 gm of fresh baker's yeast or 23 gm of instant dry baker's yeast), 20 gm of salt, 40 gm of fat and 75 gm of a baking additive for packaged, sliced bread dough with a mold-protective agent (calcium propionate). The dough was at a temperature of 30° C. 250 gm batches of the dough were incubated in a Brabender Fermentograph for 50 minutes at 30° C. The results for the leavening activity obtained are entered in Table 2 below.

TABLE 2

Comparison of the Leavening Activity of Commercial Fresh Baker's Yeast with That of Instant Dry Baker's Yeast in a Dough for Packaged, Sliced Bread Containing Mold Protective Agent

|  | Leavening Activity ml $CO_2$/50 min. |
|---|---|
| Fresh baker's yeast A | 600 |
| Fresh baker's yeast B | 630 |
| Instant dry baker's yeast C | 360 |
| Instant dry baker's yeast D | 380 |
| Comparison: Fresh baker's yeast A without the baking additive with mold protective agent | 1400 |

The Table shows that good quality fresh baker's yeasts have approximately 40% more leavening power than dry baker's yeast, based on the quantity of dry substance, in a dough for packaged, sliced bread containing commercial baker's additive with a mold protective agent. The substitution of one part of dry baker's yeast (content of dry substance 95%) for 3.16 parts of fresh baker's yeast (content of dry substance 30%), which is theoretically possible, is in this case reduced to a substitution in the proportions of 1:2 in order to obtain the same leavening power.

OBJECTS OF THE INVENTION

An object of the present invention is the development of compressed baker's yeast or dried baker's yeast having a high leavening power in the presence of acid doughs and doughs with a content of mold protective agents.

Another object of the present invention is the development of a process for the production of baker's yeast with improved activity or leavening power under acid leavening conditions of the compressed yeast or dried yeast type, comprising cultivating fresh yeast conventionally to the last propagation stage, propagating the fresh yeast in the last propagation stage in the presence of from 0.1 gm to 10 gm per liter of culture broth containing a source of carbon and nitrogen, of an aliphatic carboxylic acid having from 2 to 4 carbon atoms, and recovering baker's yeast with improved activity or leavening power.

A further object of the present invention is the obtaining of baker's yeast with improved activity or leavening power under acid leavening conditions, of the compressed yeast type or dried yeast type, produced by the above process.

These and other objects of the invention will become more apparent as the description thereof proceeds.

DESCRIPTION OF THE INVENTION

A process for the preparation of compressed yeast (fresh baker's yeast) and dry baker's yeast with improved activity or leavening power in an acid medium has now been found, in which the yeast is cultivated and worked up in the usual manner but from 0.1 to 10 gm of aliphatic short chain carboxylic acids are added per liter of culture broth in the last stage of propagation. More particularly, the present invention involves a process for the production of baker's yeast with improved activity or leavening power under acid leavening conditions of the compressed yeast or dried yeast type, comprising cultivating fresh yeast conventionally to the last propagation stage, propagating the fresh yeast in the last propagation stage in the presence of from 0.1 gm to 10 gm per liter of culture broth containing a source of carbon and nitrogen, of an aliphatic carboxylic acid having from 2 to 4 carbon atoms, and recovering baker's yeast with improved activity or leavening power; as well as the yeast produced by the above method.

The fresh baker's yeast obtained by this process is found to have a high leavening activity even in doughs with a high degree of acidity. This yeast can be converted into a durable dry baker's yeast which, like fresh baker's yeast, has an improved leavening activity in highly acid doughs.

Fresh baker's yeast is normally prepared by a multistage fermentation process. A stage of pure culture is followed by several stages of propagation with or without the formation of ethyl alcohol. The last stage of propagation, the so-called transportable yeast fermentation, is generally controlled so as to prevent the formation of ethyl alcohol from the substrate. By the addition of from 0.1 to 10 gm of aliphatic short chain carboxylic acids, especially those having from 2 to 4 carbon atoms, such as alkanoic acids like acetic acid and propionic acid, hydroxyalkanoic acids like lactic acid, hydroxyalkanedioic acids like tartaric acid and tartronic acid, etc., in particular propionic acid, per liter of culture broth in the last stage of propagation of the baker's yeast, a yeast is obtained which, when subsequently used as fresh baker's yeast or dry baker's yeast in doughs with a high degree of acidity, is found to have a substantially increased leavening activity. This yeast has a solids content after pressure filtration of about 25% to 30% by weight.

As already mentioned, the increased leavening activity is preserved even after the fresh baker's yeast has been converted into dry baker's yeast by a drying process. This drying process is particularly advantageous, and the initial activity is substantially preserved, if the fresh baker's yeast is not obtained with the addition of sodium chloride as dewatering agent or hypertonic agent but with the addition of glycerol and/or urea or other nonionic dewatering or hypotonic agents. When the fresh yeast is processed with the addition of from 0.1% to 10%, preferably from 1% to 3%, based on the dewatered yeast, or a nonionic dewatering agent and pressure filtered, a yeast is recovered with a solids content of from 30% to 37% by weight.

When the fresh yeast is worked up into dry baker's yeast, it has also been found advantageous to dry the yeast in a fluidized bed after the addition thereto of an emulsion of fat, emulsifier and water. The best results in the preparation of dry baker's yeast are obtained if the yeast is granulated and dried after the addition of from 0.5% to 5%, preferably 1% to 2.5% by weight, based on the dewatered weight of yeast, of the above emulsion. The fat employed is preferably a liquid fat such as soybean oil. The emulsifiers are esters of saturated fatty acids, such as fatty acid esters of sorbitan, e.g. sorbitan monolaurate, monopalmitate, monostearate or monooleate; fatty acid esters of glycerol, e.g., glyceryl monostearate, a distearate or monopalmitate; fatty acid esters of propylene glycol, e.g., propylene glycol monostearate; citric acid esters of the partial glycerides, e.g. glyceryl monostearate citrate; fatty acid esters of lactoyl-lactates, e.g. calcium stearoly lactoyl lactate or mixtures of two or more of the above-mentioned compounds. The emulsions preferably contain about a 1:1:2 ratio of fat, emulsifier and water but variations can occur. Preferably an emulsion of soybean oil, monoglyceride citrate, calcium stearoyl lactoyl lactate and water is employed.

The following Examples serve to explain the subject of the invention in more detail without restricting it.

EXAMPLE 1 (Prior Art)

4 Liters of tap water were introduced into a 10 liter fermenter and 250 gm of commercial fresh baker's yeast containing 29% of dry substance were suspended therein. 15 gm of potassium dihydrogen phosphate, 1 gm of calcium chloride and 1 mg of biotin were also added. The temperature was maintained at 30° C. and the mixture was stirred with a stirrer at a speed of 600 r.p.m. The supply of air to the culture broth was adjusted to 5 liters of air per minute. The addition of the carbon source and the nitrogen source to the culture broth was controlled by a programming device. 1.0 kg of beet molasses, diluted with water, and 70 ml of a 25% ammonia solution were added within 12 hours. The rate of addition of nutrient was adjusted so that at no point in time during the fermentation did the culture broth contain more than 0.1% of ethanol. The pH was maintained at 5.0 by an automatic titration apparatus. The development of foam was regulated by the addition of a commercial anti-foam agent.

After 12 hours, the quantity of substance in the fermenter had risen to 6.6 liters and the yeast biomass had increased to 1,280 gm (yeast containing 27% of dry substance).

The supply of air to the culture broth was continued for 30 minutes at the elevated temperature of 35+ C. and the yeast was then separated from the culture broth by centrifuging, washed twice with water and filtered from the washing liquor through a pressure filter operating at 2.5 bar. The dry substance in the fresh baker's yeast was determined and the appropriate quantity of yeast was used for preparing the doughs. The leavening power of the fresh baker's yeast obtained is substantially equal to that of ordinary fresh baker's yeast available on the market (see Table 3) since the usual method of fermentation was also used for its preparation.

EXAMPLE 2

Yeast fermentation was carried out as in Example 1. However, 6 gm of acetic acid were introduced into the fermenter during fermentation (in the 9th hour after onset of the addition of nutrient). The procedure was then continued as described in Example 1. The yeast obtained shows significantly improved leavening activity in doughs containing added carboxylic acid salts (see Table 3).

EXAMPLE 3

Fermentation of yeast was carried out as in Example 1. During the fermentation (in the 9th hour after onset of the addition of nutrient), 6 gm of propionic acid were introduced into the fermenter. The procedure was then continued as described in Example 1. The yeast obtained has an even better leavening activity in doughs containing added carboxylic acid than the yeasts obtained in Examples 1 and 2 (see Table 3).

LEAVENING TESTS

To carry out the leavening tests, 1.35 gm of the yeasts from Examples 1, 2 and 3 (based on the dry substance of yeast) was made up into a dough with 280 gm of wheat flour, 3.9 gm of salt and 156 ml of tap water. The water used was previously warmed so that the dough had a temperature of 30° C. after it had been kneaded for 5 minutes. One portion was in each case measured without the addition of calcium propionate and another portion with the addition of 0.5% of calcium propionate, based on the quantity of flour used. The leavening activity of the yeast was determined over a period of 2 hours at 30° C. in a Brabender Fermentograph and is given in terms of ml of carbon dioxide (see Table 3). For the experiment with baking additive for dough for packaged, sliced bread, 21 gm of a commercial baking additive containing about 10% of propionate (about 0.75% propionate) was used for preparing the dough. The leavening activities obtained are shown in Table 3.

TABLE 3

Improvement in Leavening Activity of Fresh Baker's Yeast by Final Fermentation in the Presence of a Carboxylic Acid

| Compressed Yeast From Example | ml of $CO_2$ after 2 hours | | |
|---|---|---|---|
| | Dough without additive | Dough with 0.5% calcium propionate | Dough with baking additive containing propionate |
| 1 | 1070 | 680 | 380 |
| 2 (acetic acid) | 1090 | 750 | 490 |
| 3 (propionic acid) | 1120 | 940 | 780 |

EXAMPLE 4

250 gm of fresh yeast (from Example 1) were suspended in 100 ml of 0.5% sodium chloride solution and filtered through a pressure filter at 2.5 bar. The filter cake was washed with 100 ml of water and the content of dry substance was determined. As a result of the treatment with the salt solution, which is osmotically active, the quantity of dry substance normally obtained after pressure filtration increased from 30% to 34.2%. 4 ml of an emulsion prepared from 2 parts of soybean oil, 1 part of stearoyl monoglyceryl citrate, 1 part of calcium stearoyl lactoyl lactate and 4 parts of water were added to 200 gm of the yeast from which liquid had been pressed off. The mixture of emulsion and yeast was then kneaded for 5 minutes in a kneading machine to effect thorough mixing. The yeast containing the emulsifier was then forced by means of a press through a perforated plate having 0.5 mm apertures. 100 gm of the extruded yeast was dried in a mechanically agitated fluidized bed for 15 minutes by passing air through the yeast for 8 minutes at a rate of 2 m/sec. and at a temperature of 90° C. It was then dried for 4 minutes at an air velocity of 1.5 m/sec. and a temperature of 70° C. and for 4 minutes at an air velocity of 0.9 m/sec. at 55° C. The temperature of the product was 28° C. at the beginning of drying and rose to 40° C. at the end of drying. Air which had been pre-dried over silica gel was used in the last drying stage to obtain a sufficiently dry product. This treatment increased the dry substance of the yeast from 34.2% to 95.3%. The pale colored granulate obtained had a particle diameter of 0.4 mm and was used in activity tests without further treatment.

The leavening activity of the dry baker's yeast obtained is shown in Table 4 below.

EXAMPLE 5

250 gm of fresh yeast (from Example 1) were resuspended in 100 ml of 5% glycerol solution and filtered through a pressure filter at 2.5 bar. The filter cake was not washed but was stored for 24 hours at 4° C. and then mixed with emulsifier and treated as in Example 4. The leavening activity of the dry baker's yeast obtained in this way is also shown in Table 4.

EXAMPLE 6

250 gm of fresh yeast from Example 2 were resuspended in 100 ml of 5% glycerol solution and subsequently treated as described in Example 5. The leavening activity of the resulting dry yeast in doughs to which short chain carboxylic acids have been added is considerably better than that of the dry yeasts from Examples 4 and 5 which have been obtained from a fresh yeast prepared by a conventional process of fermentation.

EXAMPLE 7

250 gm of fresh yeast from Example 3 were resuspended in 100 ml of 5% glycerol solution and subsequently treated as described in Example 5. The leavening activity of the resulting dry yeast in doughs to which short chain carboxylic acids have been added is very substantially improved, not only compared with that of the dry yeasts from Examples 4 and 5 obtained from a fresh yeast which has been prepared by a conventional fermentation process but also compared with that of the dry yeast from Example 6 which has been obtained from a fresh yeast which has been fermented with acetic acid in the last fermentation process. When used in doughs containing short chain carboxylic acids, the dry baker's yeast obtained according to this example has substantially the same activity as a fresh baker's yeast, based on the same quantity of yeast.

The doughs required for carrying out the experiments were prepared in the same way as described in the leavening tests after Example 3 and the measurements of leavening activity were also carried out in the same way.

TABLE 4

Improvement in Leavening Activity of Active Dry Baker's Yeast Prepared from Compressed Yeasts with Final Fermentation in the Presence of Carboxylic Acid

| Dry Yeast from Example | Content of dry substance in yeast in % | ml of $CO_2$ after 2 hours | | |
|---|---|---|---|---|
| | | dough without additive | dough with 0.5% calcium propionate | dough with baking additive containing propionate |
| 4 | 95.3 | 940 | 280 | 330 |
| 5 | 95.1 | 1160 | 390 | 430 |
| 6 (acetic acid) | 95.0 | 1140 | 480 | 510 |
| 7 (propionic acid) | 96.6 | 1100 | 690 | 780 |

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A process for the production of baker's yeast with improved activity or leavening power under acid leavening conditions, comprising cultivating fresh baker's yeast through a plurality of propagation stages, and in only the last propagation stage, propagating the fresh baker's yeast in the presence of from 0.1 gm to 10 gm per liter of culture broth containing a source of carbon and nitrogen, of an aliphatic carboxylic acid having from 2 to 4 carbon atoms selected from the group consisting of alkanoic acids, hydroxyalkanoic acids and hydroxyalkanedioic acids, and recovering baker's yeast having said improved activity or leavening power.

2. The process of claim 1 wherein said aliphatic carboxylic acid having from 2 to 4 carbon atoms in propionic acid.

3. The process of claim 1 wherein said aliphatic carboxylic acid having from 2 to 4 carbon atoms is acetic acid.

4. The process of claim 1 wherein baker's compressed yeast is recovered.

5. The process of claim 1 wherein baker's dried yeast is recovered.

* * * * *